United States Patent
Armengaud et al.

(10) Patent No.: US 9,765,344 B2
(45) Date of Patent: Sep. 19, 2017

(54) METHOD FOR ENHANCING THE FERMENTATIVE POTENTIAL AND GROWTH RATE OF MICROORGANISMS UNDER ANAEROBIOSIS

(75) Inventors: Jean Armengaud, Villeuve-lez-Avignon (FR); Geremy Clair, Cabannes (FR); Catherine Duport, Le Thor (FR)

(73) Assignee: Commissariat à l'énergie atomique et aux énergies alternatives, Paris (FR)

( * ) Notice: Subject to any disclaimer, the term of this patent is extended or adjusted under 35 U.S.C. 154(b) by 47 days.

(21) Appl. No.: 14/124,471

(22) PCT Filed: Jun. 5, 2012

(86) PCT No.: PCT/EP2012/060624
§ 371 (c)(1),
(2), (4) Date: Feb. 25, 2014

(87) PCT Pub. No.: WO2012/168257
PCT Pub. Date: Dec. 13, 2012

(65) Prior Publication Data
US 2014/0227749 A1   Aug. 14, 2014

(30) Foreign Application Priority Data

Jun. 6, 2011 (EP) ..................................... 11352006

(51) Int. Cl.
*C12N 15/75* (2006.01)
*C07K 14/195* (2006.01)
(Continued)

(52) U.S. Cl.
CPC ............ *C12N 15/75* (2013.01); *C07K 14/195* (2013.01); *C07K 14/32* (2013.01); *C12N 1/20* (2013.01); *C12P 7/065* (2013.01); *Y02E 50/17* (2013.01)

(58) Field of Classification Search
CPC ........ C12N 15/75; C12N 1/20; C07K 14/195; C07K 14/32; C12P 7/065; Y02E 50/17
See application file for complete search history.

(56) References Cited

U.S. PATENT DOCUMENTS

2007/0248581 A1   10/2007   Chen et al.
2009/0221027 A1   9/2009   Zelder et al.
2011/0104733 A1   5/2011   Marecat et al.

FOREIGN PATENT DOCUMENTS

FR   2 635 788   3/1990
FR   2 778 922   11/1999
(Continued)

OTHER PUBLICATIONS

PSI-Blast (last viewed on Jan. 7, 2016).*
(Continued)

*Primary Examiner* — Alexander Kim
(74) *Attorney, Agent, or Firm* — Oblon, McClelland, Maier & Neustadt, L.L.P.

(57) ABSTRACT

The present invention concerns a method for enhancing the growth rate, the biomass production and/or the fermentative potential of an anaerobic microorganism, comprising the steps consisting in: (a) modifying said anaerobic microorganism by inactivating the ohrR gene, the ohrR gene product or homolog thereof; (b) culturing the modified anaerobic microorganism obtained in step (a) under low-ORP anaerobic conditions.

16 Claims, 1 Drawing Sheet

(51) Int. Cl.
C07K 14/32 (2006.01)
C12N 1/20 (2006.01)
C12P 7/06 (2006.01)

(56) References Cited

FOREIGN PATENT DOCUMENTS

| WO | 2007 011845 | | 1/2007 |
|---|---|---|---|
| WO | 2007 090123 | | 8/2007 |
| WO | WO 2009/101328 A1 | | 8/2009 |
| WO | WO2009/143495 | * | 11/2009 |
| WO | WO 2011/006136 A2 | | 1/2011 |
| WO | WO 2011/018116 A1 | | 2/2011 |

OTHER PUBLICATIONS

Chatterjee et al., Intracellular Gene Expression Profile of Listeria Monocytogenes., Infection and Immunity (2006), vol. 74, pp. 1323-1338.*
Lungu et al., Growth, survival, proliferation and pathogenesis of Listeria monocytogenes under low oxygen or anaerobic conditions: A review, Anaerobe (2009), vol. 15, Issues 1-2, pp. 7-17.*
Chuchue et al., ohrR and ohr are the primary sensor/regulator and protective genes against organic hydroperoxide stress in Agrobacterium tumefaciens., J Bacteriol. (2006), vol. 188(3), pp. 842-851.*
Fuangthong et al., OhrR is a repressor of ohrA, a key organic hydroperoxide resistance determinant in Bacillus subtilis., J Bacteriol. (2001), vol. 183(14), pp. 4134-4141.*
Clair, G. et al., "Restricting Fermentative Potential by Proteome Remodeling", Molecular & Cellular Proteomics, vol. 11, No. 6, Total 13 Pages, (Jan. 9, 2012) XP009161847.
Arntjen, B. et al., "Impact of MarA Point Mutations on Growth Rate and Susceptibilities to Different Antibiotics of in vitro Generated Mutants of E.coli with Mar Phenotype", Internatioanl Journal of Medical Microbiology, vol. 299, No. Suppl. 1, p. 82, (Sep. 1, 2009) XP009153673.
Cano, D. A. et al., "*Salmonella enterica* Serovar Typhimurium Response Involved in Attenuation of Pathogen Intracellular Proliferation", Infection and Immunity, vol. 69, No. 10, pp. 6463-6474, (Oct. 1, 2001) XP055011125.
Ellison, D. et al., "Regulation of virulence by members of the MarR/SlyA family", Current Opinion in Microbiology, vol. 9, No. 2, pp. 153-159, (Apr. 1, 2006) XP025174542.
Fuangthong, M. et al., "OhrR Is a Repressor of ohrA, a Key Organic Hydroperoxide Resistance Determinant in Bacillus subtilis", Journal of Bacteriology, vol. 183, No. 14, pp. 4134-4141, (Jul. 15, 2001) XP055011126.
Hong, M. et al., "Structure of an OhrR-ohrA Operator Complex Reveals the DNA Binding Mechanism of the MarR Family", Molecular Cell, vol. 20, No. 1, pp. 131-141, (Oct. 7, 2005) XP055011130.
Soonsanga, S. et al., "Mutational Analysis of Active Site Residues Essential for Sensing of Organic Hydroperoxides by Bacillus subtilis OhrR", Journal of Bacteriology, vol. 189, No. 19, pp. 7069-7076, (Oct. 1, 2007) XP055011132.
Duarte, V. et al., "PerR vs OhrR: selective peroxide sensing in Bacillus subtilis", Molecular Biosystems, vol. 6, No. 2, pp. 316-323, (Jan. 1, 2010) XP009153352.
Martin, R. G. et al., "Transcriptional and translational regulation of the marRAB multiple antibiotic resistance operon in *Escherichia coli*", Molecular Microbiology, vol. 53, No. 1, pp. 183-191, (Jul. 1, 2004) XP055011134.
Clair, G. et al.. "Expanding the Known Repertoire of Virulence Factors Produced by Bacillus cereus through Early Secretome Profiling in Three Redox Conditions", Molecular & Cellular Proteomics, vol. 9, No. 7, pp. 1486-1498, (Jul. 1, 2010) XP055011137.
International Search Report Issued Aug. 21, 2012 in PCT/EP12/060624 Filed Jun. 5, 2012.
European Search Report issued Nov. 10, 2011, in Patent Application No. EP 11 35 2006.
Catherine Duport, et al., "Control of Enterotoxin Gene Expression in Bacillus cereus F4430/73 Involves the Redox-Sensitive Sensitive ResDE Signal Transduction System", Journal of Bacteriology, vol. 188, No. 18, 2006, pp. 6640-6651.
Hong Gao, et al., "Engineering of a genome-reduced host: practical application of synthetic biology in the overproduction of desired secondary metabolites", Protein & Cell, vol. 1, 2010, pp. 621-626.
Daniel G. Gibson, et al., "Creation of a Bacterial Cell Controlled by a Chemically Synthesized Genome", Science, vol. 329, Jul. 2010, pp. 52-56.
J. Sambrook, et al., "Molecular Cloning", (A Laboratory Manual, second edition), Cold Spring Harbor Laboratory Press, 1989, 34 pages.
Michael D. Dambach, et al., "Expanding roles for metabolite-sensing regulatory RNAs", Current Opinion in Microbiology, (Elsevier), vol. 12, 2009, pp. 161-169.
Tina M. Henkin, Riboswitch RNAs: using RNA to sense cellular metabolism, Genes& Development, vol. 22, 2008, pp. 3383-3390.
Mongkolsuk et al, "Regulation of inducible peroxide stress responses", Molecular Microbiology, vol. 45, pp. 9-15, 2002.
Mongkolsuk et al., "Identification and Characterization of a New Organic Hydroperoxide Resistance (ohr) Gene with a Novel Pattern of Oxidative Stress Regulation from *Xanthomonas campestris* pv. Phaseoli", Journal of Bacteriology. vol. 180, No. 10, pp. 2636-2643, May 1998.
Sukchawalit et al., "Complex Regulation of the Organic Hydroperoxide Resistance Gene (ohr) from *Xanthomonas* Involves OhrR, a Novel Organic Peroxide-Inducible Negative Regulator, and Posttranscriptional Modifications", Journal of Bacteriolology, vol. 183, No. 15, pp. 4405-4412, 2001.
Fuangthong et al., "The OhrR repressor senses organic hydropoeroxides by reversible formation of a cysteine-sulfenic acid derivative", PNAS. vol. 99, No. 10, pp. 6690-6695, 2002.
Soonsanga, et al., "Mutational Analysis of Active Site Residues Essential for Sensing of Organic Hydroperoxides by *Bacillus subtilis* OhrR", Journal of Bacteriology, vol. 189, No. 19, pp. 7069-7076, 2007.
Panmanee, et al., "OhrR, a transcription repressor that senses and responds to changes in organic peroxide levels in *Xanthomonas campestris* pv. Phaseoli", Molecular Microbiology, vol. 45, No. 6, pp. 1647-1654. 2002.

* cited by examiner

METHOD FOR ENHANCING THE FERMENTATIVE POTENTIAL AND GROWTH RATE OF MICROORGANISMS UNDER ANAEROBIOSIS

TECHNICAL FIELD

The present invention belongs to the technical field of methods using microorganisms and, in particular, of methods using genetically modified microorganisms that have enhanced fermentation activity and/or enhanced growth rate in selected particular culture conditions.

The present invention proposes a method that results in a genetically modified strain exhibiting higher anaerobic growth rate using basically the same culture condition as the wild-type strain. More particularly, the present invention method is based on the abolishment of the synthesis of a protein that is substantially similar to *Bacillus cereus* OhrR (for "Organic hydroperoxide resistance Regulator").

The present invention relates to a method for increasing the fermentative potential and/or the growth rate of a microorganism under low Oxido-Reduction Potential (low-ORP) anaerobic culture conditions.

STATE OF THE PRIOR ART

Nowadays many microorganisms are implemented for different industrial applications. Fields of application are covering industrial processes related to human or animal health (red biotechnology); agro-industries, agronomy and farming (green biotechnology); marine and aquatic processes (blue technology); chemical industry (white biotechnology); energy industry and, in particular, biomass conversion field; environmental processes such as bioremediation, water and industrial fluid purification, $CO_2$ captation, etc. . . . . Most of these processes use the ability of microorganisms to produce cell biomass, proteins and/or primary/secondary metabolites.

As for examples, microorganisms can be used in the production of food products such as wine or beer; in the production of biofuels, notably by the conversion of sugar into ethanol; in the pharmaceutical field to produce active ingredients such as antibiotics or insulin; in the production of valuable chemicals or in the destruction of hazardous and/or polluting chemicals.

As a consequence, there is a real need to propose methods that make it possible to obtain an enhanced production and/or an enhanced production yield in the processes using microorganisms.

This technical problem can be solved by selecting appropriate culture conditions. Thus, international application WO 2009/101328 [1] proposes a method for culturing microorganisms in order to increase their biomass and their metabolic activity. The method disclosed consists in a combined adjustment of the Oxidation-Reduction Potential (ORP) and the dissolved oxygen. Indeed, the inventors of this application have noted that using a strain of *Lactococcus lactis* as microorganisms and adjusting simultaneously the redox potential within the range extending from −400 to 0 mV and the dissolved oxygen value within the range extending from 1 to 30%, large gains are obtained in biomass and acidifying activity. Nevertheless, the main drawbacks of the process disclosed in [1] concern the fact that it can only be implemented with facultative anaerobe or aerobe strains because of the presence of dissolved oxygen and that it requires the continuous adjustment of parameters which influence each other.

Alternatively, the above-identified technical problem can be solved by identifying and using microorganisms which present enhanced production, enhanced production yield and/or enhanced growth rate, when compared to the microorganisms implemented until now in the above-listed processes. Most of the time, these microorganisms are genetically modified.

Among the different studies already disclosed on such microorganisms, one can cite the patent applications FR 2 635 788 [2] and FR 2 778 922 [3]. The former concerns the use of a nucleic acid comprising a functional nucleotide sequence contained in a 14 kb fragment obtained from the chromosome of a *Bacillus subtilis* strain having a $sacU^h$ mutation. Once introduced into *B. subtilis* or into any other microorganism, said sequence is capable of exploiting to its advantage the information carried by this fragment, of inducing therein an overproduction of proteins or of conferring on it a $Deg^h$ phenotype [2]. The patent application FR 2 778 922 discloses the use of a polynucleotide comprising all or part of at least one regulatory sequence of a *Clostridium* toxin synthesis operon to modify *Clostridium* or *Escherichia coli* and to promote the synthesis of a homologous or heterologous protein therein [3].

International application WO 2011/018116 [4] proposes a metabolically enhanced photoautotrophic, ethanol producing host cell comprising: (1) at least two first metabolic enhancements reducing the enzymatic activity or affinity of at least two endogenous host cell enzymes involved in acetate and lactate fermentation, the first metabolic enhancements resulting in an enhanced level of biosynthesis of acetaldehyde, pyruvate, acetyl-CoA or precursors thereof compared to the respective wild type host cell, (2) at least one second metabolic enhancement different from the first metabolic enhancement comprising an overexpressed enzyme for the formation of ethanol. The host cell implemented in this method is a prokaryotic cell and advantageously a cyanobacterial cell.

Moreover, international application WO 2011/006136 [5] proposes a method for producing ethanol, ethanol derivatives, ethanol conjugates and/or other organic chemical intermediates using biological system. This latter consists in a microorganism strain and, in particular, a *Sacharomyces cerevisiae* strain or a bacterium that includes an alteration that adds or increases a phosphogluconate dehydratase activity, a 2-keto-3-deoxygluconate-6-phosphate aldolase activity and a xylose isomerase activity.

It must be pointed out that some of the genetically-modified microorganisms used in the above-cited prior art only make it possible to enhance the production of particular proteins and/or of particular primary/secondary metabolites. Other genetically-modified microorganisms require several genetic modification steps to be prepared.

DISCUSSION OF THE INVENTION

The present invention based on unexpected data recorded by the inventors makes it possible to solve the above-identified technical problem and some drawbacks of the prior art methods.

Indeed, the present inventors have worked on *Bacillus cereus* that is a motile facultative anaerobe responsible of diarrhoeal disease in humans. To survive in the gastrointestinal tract and initiate infection, this microorganism is able to adapt to variable oxygen and oxidoreduction potential (ORP) conditions by modulating its central metabolic pathways [6].

Consequently, the present inventors have been aimed at elucidating the regulatory mechanisms tuning these pathways. They have shown that a dominant component of these regulatory mechanisms involves whole proteome remodeling that restricts fermentative potential while boosting motility, respiratory potential and oxidative stress resistance. Specifically, gene inactivation studies and high-throughput proteome analyses have identified organic hydroxyperoxide resistance (Ohr)-homologous proteins, OhrA (for "Organic hydroxyperoxide resistance A") and OhrR, as key players of the proteome remodeling occurring in response to oxygen availability and extracellular ORP changes.

In addition and unexpectedly, the present inventors have noted that disruption of ohrR gene leads to a significant increase (56%±10%) of the growth rate of fermentative cells under low-ORP anaerobic conditions compared with wild-type cells and no significant difference can be observed under high-ORP anaerobiosis and aerobiosis. On the contrary, the growth rate of the ΔohrA mutant is significantly lower than that of the wild-type under aerobiosis (−29%±3%) and in a lesser extent under anaerobiosis (−22%±2%).

Thanks to these results, the inventors have identified that the combination of a particular microorganism i.e. a ΔohrR mutant and of particular culture conditions i.e. low-ORP anaerobic conditions makes it possible to obtain a strain with enhanced growth rate and enhanced fermentative potential, when compared with the growth rate and the fermentative potential of the wild-type strain, i.e. the non mutated strain, grown in the same culture conditions.

A key advantage of this modified strain compared with the wild-type strain is that the anaerobic growth rate in low-ORP condition can be significantly increased without modifying substantially the growth conditions, resulting in the production of higher levels of biomass in less time. Another aspect of the invention is to achieve higher growth rate of the modified strain in low-ORP anaerobic conditions compared with high-ORP anaerobic conditions.

In addition, since *B. cereus* OhrR homologues are present in many microorganisms used or susceptible to be used in industrial applications, the process described here can be applied to many microorganisms in order to improve the production of cell biomass, proteins, or primary/secondary metabolites; or increase the yield of any process into which these microorganisms are used.

The inventors have also noted that ohrR disruption strongly decreases the abundance level of twelve flagellar and chemotaxis-related proteins besides OhrA. Thus the ohrR mutant presents a decreased motility which can be an additional advantage when using the strain in decontamination process. Indeed, in such processes, strains which stay where they have been inoculated are preferred.

Thus, the present invention concerns a method for enhancing the growth rate, the biomass production and/or the fermentative potential of an anaerobic microorganism, comprising the steps consisting in:

a) modifying said anaerobic microorganism by inactivating the ohrR gene, the ohrR gene product or homolog thereof;

b) culturing the modified anaerobic microorganism obtained in step (a) under low-ORP anaerobic conditions;

in consideration of which (or in view of which or thereby) the growth rate, the biomass production and/or the fermentative potential of said modified microorganism is enhanced when compared with the growth rate, the biomass production and/or the fermentative potential of the corresponding non modified microorganism cultured under the same conditions.

For microorganisms, growth results in an increase in the number of individuals. This increase comes from one cell division into two new cells. In the present invention, the growth rate can be determined by different experimental methods.

Indeed, the growth rate can be determined by counting the number of microorganisms. More particularly, a volume v of the microorganism culture is taken after a time t of culture under low-ORP anaerobic conditions in a medium m, the number of microorganisms is manually counted in this volume v thanks to a microscope (Petroff-Hausser counting chamber) or thanks to electronic counters such as Coulter counter.

The growth rate can also be determined by measuring the turbidity of the microorganism culture. More particularly, a volume v of the microorganism culture is taken after a time t of culture under low-ORP anaerobic conditions in a medium m. The turbidity of this volume v is measured thanks to a turbidimeter or a colorimeter typically at a wavelength of 560 nm.

Alternatively, the growth rate can be determined by plate counting of CFU (for "Colony Forming Unit"). In practice, a volume v of the microorganism culture optionally diluted is spread on the surface of solidified nutrient medium for example agar with 4% glucose, which when incubated, leads to each cell developing into a visible colony through repeated fission. After incubation during a time t, all colonies formed are counted and the number of CFU in the volume v is calculated.

When comparing the growth rate of the modified microorganism implemented in the present invention with the non modified corresponding microorganism, it is clear that both growth rates must be measured thanks to the same method, in an identical volume v of microorganism culture after an identical time t of culture under identical low-ORP anaerobic conditions in an identical medium m, modified and non modified microorganisms having been seeded in the medium m at the same concentration.

The biomass production can be determined by measuring the dry weight of the microorganism culture. More particularly, a volume v of the microorganism culture is taken after a time t of culture under low-ORP anaerobic conditions in a medium m. This volume v is dried for example at 110° C. during 12 h, then the dried sample thus obtained is weighed.

When comparing the biomass production of the modified microorganism implemented in the present invention with the non modified corresponding microorganism, it is clear that both biomass productions must be measured in an identical volume v of microorganism culture after an identical time t of culture under identical low-ORP anaerobic conditions in an identical medium m, modified and non modified microorganisms having been seeded in the medium m at the same concentration.

In addition, once the biomass production has been obtained, the specific growth rate dy/dt can be calculated from the growth curve which was modelized using the modified Gompertz equation:

$$y=A\exp\{-\exp[(\mu_m\cdot e/A)(\lambda-t)+1]\},$$

wherein y is the biomass production (in $g\cdot l^{-1}$), $\mu_m$ the maximum specific growth rate (in $h^{-1}$), λ the lag time (in h), A and e, the mathematical parameters describing the sigmoidal growth curve and t the time (in h).

The fermentative potential is representative of the catabolic activity of the anaerobic microorganism. The fermentative potential can be determined by measuring the quantity of a particular element in the microorganism culture. Said particular element which can be a metabolite must be representative of the fermentative activity of the microorganism. In other words, the particular element is a molecule produced by the microorganism when submitted to the low-ORP anaerobic conditions. As for examples, one can cite ethanol, acetate, formate, lactate, acetoin, butanediol and $CO_2$. Clearly, this particular element will depend on the microorganism implemented in the present invention.

More particularly, a volume v of the microorganism culture is taken after a time t of culture under low-ORP anaerobic conditions in a medium m and the quantity of the particular element is quantified in the volume v. This quantification is carried out by using commercial kits or methods well-known by the one skilled in the art.

When comparing the fermentative potential of the modified microorganism implemented in the present invention with the non modified corresponding microorganism, it is clear that both fermentative potentials must be measured in an identical volume v of microorganism culture after an identical time t of culture under identical low-ORP anaerobic conditions in an identical medium m, modified and non modified microorganisms having been seeded in the medium m at the same concentration.

The one skilled in the art will choose the appropriate time t and the appropriate volume v to conduct any comparison between the modified microorganism and the non modified microorganism, according to these microorganisms and the medium implemented.

In the context of the present invention, only one of the parameters chosen from the growth rate, the biomass production and the fermentative potential can be enhanced in the modified microorganism when compared to the non modified microorganism.

Alternatively, two of these parameters, i.e. growth rate and biomass production; growth rate and fermentative potential; biomass production and fermentative potential, can be enhanced in the modified microorganism when compared to the non modified microorganism.

Alternatively again, the three parameters can be enhanced in the modified microorganism when compared to the non modified microorganism.

The term "enhanced" means that the growth rate, the biomass production or the fermentative potential is increased and, in particular, significantly increased when the value ($V_1$) of one of these parameters determined for the modified microorganism is compared to the value ($V_2$) of the corresponding parameter determined for the non modified corresponding microorganism. This increase (I) of formula (I)=[($V_1-V_2$)/$V_2 \times 100$] can be superior or egal to 10%, notably superior or egal to 20%, in particular, superior or egal to 40% and, more particularly, superior or egal to 50%.

An anaerobic microorganism is a microorganism that thrives in oxygen-deprived areas and its growth in oxygen-proficient areas is severely limited.

The anaerobic microorganism which can be used in the method according to the present invention can be a facultative anaerobic microorganism or an obligate anaerobic microorganism. A facultative anaerobic microorganism makes ATP by aerobic respiration if oxygen is present but is also capable of switching to fermentation in the absence of oxygen or to anaerobic respiration in the absence of oxygen and in the presence of at least one external electron acceptor such as nitrates. In contrast, an obligate anaerobic microorganism is incapable of aerobic respiration.

The anaerobic microorganism which can be used in the method according to the present invention can be any natural, genetically-modified or synthetic, eukaryotic or prokaryotic, anaerobic microorganism. Advantageously, the anaerobic microorganism which can be used in the method according to the present invention can be any natural, genetically-modified or synthetic, prokaryotic, anaerobic microorganism. For example, a suitable anaerobic microorganism can be an anaerobic bacteria and notably a facultative anaerobic bacteria or an obligate anaerobic bacteria.

By "genetically-modified microorganism", it must be understood that the microorganism can have already been genetically modified before the inactivation of the ohrR gene, of the ohrR gene product or of the homolog thereof. As used herein, the expressions "genetically-modified" and "genetically-engineered" are equivalent and can be used interchangeably.

This genetic modification can consist in inserting a gene or a particular polynucleotide sequence in the microorganism to confer a particular property to the microorganism such as the capacity of utilizing carbohydrates or to activate the activity for which this gene or this particular polynucleotide sequence encodes, such as the expression of an enzyme. For example, this gene or this particular polynucleotide sequence encodes enzymes in a particular metabolic pathway such as in the metabolic pathway of ethanol. In this example, this gene or this particular polynucleotide sequence encodes an enzyme that metabolizes pentose and/or hexose sugars. Alternatively, this genetic modification can consist in the inactivation of a competing pathway such as a competing pathway for carbon flow by inactivating various genes. Additionally, this genetic modification can consist in confering or improving the tolerance to a particular element, such as, for example, butanol tolerance, through chemical mutagenesis and mutant screening.

By "synthetic microorganism", it must be understood a genome-reduced host constructed and engineered by synthetic biology. This synthetic microorganism is obtained by introducing selected genetic information from source organism(s) into a genetically friendlier host, also designed as "chassis" or "recipient". Particular examples of processes suitable to prepare such synthetic microorganism can be found in Gao et al., 2010 [7] and in Gibson et al., 2010 [8].

A natural, genetically-modified or a synthetic anaerobic microorganism suitable for the method according to the present invention presents an ohrR gene or a homolog thereof. This gene is designed as "native gene" or "endogenous gene". Alternatively, the selected genetic information from source organism(s) introduced into the recipient host to prepare a synthetic anaerobic microorganism can lack an ohrR gene or a homolog thereof. In this alternative, the step (a) of the method according to the present invention is carried out while preparing the synthetic anaerobic microorganism.

Suitable natural or genetically-modified microorganisms for the method of the present invention include, but are not limited to, members of the genera: *Abiotrophia, Acetivibrio, Acetobacter, Acetohalobium, Achromobacter, Acidaminococcus, Acidiphilium, Acidithiobacillus, Acidobacterium, Acidothermus, Acidovorax, Acinetobacter, Actinomyces, Actinosynnema, Aerococcus, Aeromicrobium, Aeromonas, Afipia, Agrobacterium, Alcanivorax, Algoriphagus, Alicycliphilus, Alicyclobacillus, Alkaliphilus,* alpha, *Alteromonadales, Alteromonas, Aminobacterium, Aminomonas, Amycolatopsis, Amycolicicoccus, Anabaena, Anaero-* coccus, Anaerofustis, Anaerolinea, Anaeromyxobacter, Anaerostipes, Anaerotruncus, Anoxybacillus, Archaeoglobus, Arcobacter, Aromatoleum, Arthrobacter, Asticcacaulis, Atopobium, Aurantimonas, Azoarcus, Azorhizobium, Azospirillum, Azotobacter, Bacillus, Bacteriovorax, Bacterium, Bacteroides, Bdellovibrio, Beijerinckia, Beta, Beutenbergia, Bilophila, Blastopirellula, Blautia, Bordetella, Brachyspira, Bradyrhizobium, Brevibacillus, Brevibacterium, Brevundimonas, Brucella, Bryantella, Bulleidia, Burkholderia, Burkholderiales, Butyrivibrio, Caldicellulosiruptor, Candidatus, Capnocytophaga, Carboxydothermus, Cardiobacterium, Carnobacterium, Catenibacterium, Catenulispora, Caulobacter, Cellulomonas, Cellulophaga, Cellvibrio, Chitinophaga, Chlorobaculum, Chlorobium, Chloroflexus, Chloroherpeton, Chromobacterium, Chromohalobacter, Chryseobacterium, Chthoniobacter, Citreicella, Citrobacter, Citromicrobium, Clavibacter, Clostridia, Clostridiales, Clostridium, Collinsella, Colwellia, Comamonas, Conexibacter, Congregibacter, Coprobacillus, Coprococcus, Coprothermobacter, Coraliomargarita, Corynebacterium, Coxiella, Croceibacter, Cronobacter, Cryptobacterium, Cupriavidus, Curvibacter, Cyanothece, Cytophaga, Deinococcus, Delftia, delta, Denitrovibrio, Desmospora, Desulfarculus, Desulfatibacillum, Desulfitobacterium, Desulfobacca, Desulfobacterium, Desulfococcus, Desulfohalobium, Desulfomicrobium, Desulfotalea, Desulfotomaculum, Desulfovibrio, Desulfurispirillum, Desulfuromonas, Dethiobacter, Dethiosulfovibrio, Dichelobacter, Dickeya, Dictyoglomus, Dietzia, Dinoroseobacter, Dokdonia, Dorea, Dyadobacter, Dysgonomonas, Edwardsiella, Eggerthella, Eikenella, Elusimicrobium, Enhydrobacter, Enterobacter, Enterococcus, Eremococcus, Erwinia, Erysipelotrichaceae, Erythrobacter, Escherichia, Ethanoligenens, Eubacterium, Exiguobacterium, Faecalibacterium, Ferrimonas, Ferroglobus, Fervidobacterium, Fibrobacter, Finegoldia, Flavobacteria, Flavobacteriaceae, Flavobacteriales, Flavobacterium, Fluviicola, Frankia, Fulvimarina, Fusobacterium, gamma, Gemella, Gemmata, Gemmatimonas, Geobacillus, Geobacter, Geodermatophilus, Glaciecola, Gloeobacter, Gluconacetobacter, Gordonia, Gordonibacter, Gramella, Granulicatella, Grimontia, Hahella, Halalkalicoccus, Halanaerobium, Haliangium, Halomonas, Heliobacterium, Herbaspirillum, Herminiimonas, Herpetosiphon, Hirschia, Hoeflea, Holdemania, Hylemonella, Hyphomicrobium, Hyphomonas, Idiomarina, Ilyobacter, Intrasporangium, Isosphaera, Janibacter, Jannaschia, Janthinobacterium, Jonesia, Jonquetella, Kineococcus, Kitasatospora, Klebsiella, Kluyvera, Kocuria, Kordia, Kosmotoga, Kribbella, Krokinobacter, Ktedonobacter, Labrenzia, Lachnospiraceae, Lacinutrix, Lactobacillus, Lactococcus, Lautropia, Leadbetterella, Leeuwenhoekiella, Legionella, Leptospira, Leptospirillum, Leptothrix, Leptotrichia, Leuconostoc, Limnobacter, Listeria, Lutiella, Lysinibacillus, Macrococcus, Magnetococcus, Magnetospirillum, Mahella, Maribacter, Maricaulis, Marinithermus, Marinobacter, Marinomonas, Mariprofundus, Maritimibacter, Marivirga, Megamonas, Megasphaera, Meiothermus, Mesorhizobium, Metallosphaera, Methanobacterium, Methanobrevibacter, Methanocella, Methanococcus, Methanohalophilus, Methanoplanus, Methanosarcina, Methanosphaera, Methanosphaerula, Methanospirillum, Methylibium, Methylobacter, Methylobacterium, Methylocella, Methylocystis, Methylomicrobium, Methylophaga, Methylophilales, Methylosinus, Methylotenera, Methyloversatilis, Methylovorus, Microbacterium, Micrococcus, Micromonospora, Microscilla, Mitsuokella, Moorella, Moritella, Mucilaginibacter, Mycobacterium, Mycoplasma, Myxococcus, Nakamurella, Natranaerobius, Neisseria, Nitrobacter, Nitrosococcus, Nocardia, Nocardioidaceae, Nocardioides, Nocardiopsis, Nostoc, Novosphingobium, Oceanibulbus, Oceanicaulis, Oceanicola, Oceanobacillus, Oceanobacter, Oceanospirillum, Ochrobactrum, Octadecabacter, Odoribacter, Oenococcus, Oligotropha, Olsenella, Oribacterium, Oscillatoria, Oscillochloris, Oxalobacter, Oxalobacteraceae, Paenibacillus, Paludibacter, Pantoea, Parabacteroides, Paracoccus, Paraprevotella, Parasutterella, Parvibaculum, Parvularcula, Pectobacterium, Pediococcus, Pedobacter, Pelagibaca, Pelobacter, Pelotomaculum, Peptostreptococcus, Petrotoga, Phaeobacter, Phenylobacterium, Photobacterium, Photorhabdus, Physcomitrella, Picrophilus, Pirellula, Planctomyces, Planococcus, Plautia, Polaribacter, Polaromonas, polymorphum, Polynucleobacter, Populus, Prevotella, Propionibacterium, Prosthecochloris, Providencia, Pseudoalteromonas, Pseudomonas, Pseudonocardia, Pseudoramibacter, Pseudovibrio, Pseudoxanthomonas, Psychroflexus, Psychromonas, Pusillimonas, Pyramidobacter, Rahnella, Ralstonia, Reinekea, Renibacterium, Rhizobium, Rhodobacter, Rhodobacterales, Rhodococcus, Rhodoferax, Rhodopirellula, Rhodopseudomonas, Rhodospirillum, Rhodothermus, Ricinus, Robiginitalea, Roseburia, Roseibium, Roseiflexus, Roseobacter, Roseomonas, Roseovarius, Rothia, Rubrivivax, Rubrobacter, Ruegeria, Ruminococcus, Saccharomonospora, Saccharopolyspora, Sagittula, Salinispora, Salmonella, Sanguibacter, Sebaldella, Segniliparus, Selenomonas, Serratia, Shewanella, Shigella, Shuttleworthia, Sideroxydans, Silicibacter, Simonsiella, Sinorhizobium, Slackia, Sodalis, Solibacillus, Solobacterium, Sorangium, Sordaria, Sphaerobacter, Sphingobacterium, Sphingobium, Sphingomonas, Sphingopyxis, Spirochaeta, Spirosoma, Stackebrandtia, Staphylococcus, Stappia, Starkeya, Stenotrophomonas, Stigmatella, Streptococcus, Streptomyces, Streptosporangium, Subdoligranulum, Sulfitobacter, Sulfolobus, Sulfuricurvum, Sutterella, Symbiobacterium, Synechococcus, Synechocystis, Synergistetes, synthetic, Syntrophobacter, Syntrophobotulus, Syntrophomonas, Syntrophothermus, Syntrophus, Tepidanaerobacter, Teredinibacter, Terriglobus, Thalassiobium, Thauera, Thermaerobacter, Thermincola, Thermoanaerobacter, Thermoanaerobacterium, Thermobaculum, Thermobifida, Thermobispora, Thermomicrobium, Thermomonospora, Thermoplasma, Thermosediminibacter, Thermosipho, Thermotoga, Thermotogales, Thioalkalivibrio, Thiobacillus, Thiomonas, Tolumonas, Treponema, Tsukamurella, Turicibacter, Variovorax, Veillonella, Verminephrobacter, Verrucomicrobiae, Verrucomicrobium, Verrucosispora, Vibrio, Vibrionales, Victivallis, Weissella, Wolinella, Xanthobacter, Xanthomonas, Xenopus, Xenorhabdus, Xylella, Yersinia and Zunongwangia. Indeed, in each above-listed genus, at least one representative comprises a close OhrR homologue identified using the OhrR amino acid sequence from *Bacillus cereus* by two iterations of Position Specific Iterated-BLAST (PSI-BLAST) (p value <1e-10).

Based on published results, the ohrA gene is known in bacteria as a gene coding a thiol peroxidase that catalyses the reduction of an organic hydroxyperoxide to its corresponding less harmful alcohol. The expression of this gene is strongly and selectively induced by organic peroxides. This regulation requires OhrR, an organic peroxide-inducible negative regulator belonging to the MarR family of repressor proteins [9].

In *Bacillus cereus* ATCC14579, the gene ohrR codes for the protein OhrR, the amino acid sequence of which can be obtained in the NCBI entrez database under the accession number NP_834186.1 and is the following:

```
MTEDSLHLDNQLCFSIYACSREVTRFYRPYLEEMGITYPQYITLLVLWEQ

DGLTVKEIGERLFLDSGTLTPMLKRMESLNLVKRVRSKEDERKVCIELTE

QGKDLQDKACSLPTTMATNLGITEQEYRSLLIQLNKLIETMKTINDRKGE
(SEQ ID NO: 1 in the appended sequence listing).
```

The ohrR gene product refers not only to the polypeptide or protein OhrR but also to the corresponding mRNA.

By <<homolog thereof>> it must be understood in the present invention not only a homolog of the gene ohrR of *Bacillus cereus* and, in particular, of *Bacillus cereus* ATCC14579 but also a homolog of the gene product of *Bacillus cereus* and, in particular, of *Bacillus cereus* ATCC14579.

As used in the present invention, the terms "homolog" and "homologous" refer to the relationship between genes, nucleic acids, ribonucleic acids or proteins that possess a common evolutionary origin and/or a common function, including homologous genes, nucleic acids, ribonucleic acids or proteins from different species. Such proteins and their encoding nucleic acid sequences have sequence homology, as reflected by their sequence identity, whether in terms of percent identity or similarity, or the presence of specific residues or motifs at conserved positions.

In the present application, a homolog to ohrR gene is a gene coding for an amino acid sequence identified or detected using the OhrR amino acid sequence from *Bacillus cereus* by two iterations of Position Specific Iterated-BLAST (PSI-BLAST) (p value <1e-10). Similarly, a homolog to the ohrR gene product is an amino acid sequence or a RNA coding for an amino acid sequence, wherein these amino acid sequences are identified or detected using the OhrR amino acid sequence from *Bacillus cereus* by two iterations of Position Specific Iterated-BLAST (PSI-BLAST) (p value <1e-10). In other words, when two iterations of Position Specific Iterated-BLAST (PSI-BLAST) (p value <1e-10) using the OhrR amino acid sequence from *Bacillus cereus* are implemented, the amino acid sequence of the ohrR gene product or coded by the ohrR gene product (RNA) or by the ohrR gene already present in the database used or just added therein is identified. Any database known by the one skilled in the art can be used for these iterations of PSI-BLAST (p value <1e-10). For example, one can cite the NCBI non-redundant protein sequences database (NCBInr), the reference proteins database (refseq_protein), the UniProtKB/Swiss-Prot database (swissprot), the metagenomic proteins database (NCBI env_nr).

In a specific embodiment, two genes or (ribo)nucleic acid sequences are homologous or substantially identical when at least 20%, at least 30%, at least 40%, at least 50%, at least 60%, at least 70%, at least 80%, at least 90% or at least 95%, of the (ribo)nucleotides match over the defined length of the (ribo)nucleic acid sequence, as determined by sequence comparison algorithms, such as BLAST, FASTA or DNA Strider. Sequences that are homologous can be identified by comparing the sequences using standard software available in sequence databases, or in a Southern hybridization experiment under, for example, stringent conditions. The appropriate stringency conditions for hybridizing nucleic acids in terms of temperature and of ionic strength depends on the length of the (ribo)nucleic acids and the degree of complementation. Such conditions can be easily determined by the one skilled in the art.

Similarly, in another specific embodiment, two amino acid sequences are homologous or substantially identical when at least 20%, at least 30%, at least 40%, at least 50%, at least 60%, at least 70%, at least 80%, at least 90% or at least 95% of the amino acids are identical. Advantageously, the similar or homologous amino acid sequences are identified by alignment using, for example, sequence comparison algorithms, such as BLAST, FASTA or DNA Strider.

Thus, a homolog of the ohrR gene is a gene or a nucleic acid presenting an identity in the nucleotide sequence of at least 20%, at least 30%, at least 40%, at least 50%, at least 60%, at least 70%, at least 80%, at least 90% or at least 95% with the ohrR gene nucleotide sequence of *Bacillus cereus* ATCC14579.

In addition, a homolog of the ohrR gene product is a ribonucleic acid or a polypeptide presenting an identity in the ribonucleotide or in the amino acid sequence of at least 20%, at least 30%, at least 40%, at least 50%, at least 60%, at least 70%, at least 80%, at least 90% or at least 95% with the ohrR gene product ribonucleotide or amino acid sequence of *Bacillus cereus* ATCC14579.

It must be reminded that percent identity between two (ribo)nucleotide or amino acid sequences is generally determined by aligning the residues of the two sequences to optimize the number of identical (ribo)nucleotides or amino acids along the lengths of their sequences; gaps in either or both sequences are permitted in making the alignment in order to optimize the number of identical (ribo)nucleotides or amino acids, although the (ribo)nucleotides or amino acids in each sequence must nonetheless remain in their proper order.

Advantageously, identical sequences are or encode for proteins having identical or similar function. In the present case, identical sequences should be or encode a repressor of OhrA or of a gene homolog to OhrA.

In addition, when percentage of sequence identity is used in reference to proteins, it is recognized that residue positions which are not identical often differ by conservative amino acid substitutions, where amino acid residues are substituted for other amino acid residues with similar chemical properties, such as charge, hydrophilicity or hydrophobicity, and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to the one skilled in the art. Typically this involves scoring a conservative substitution as a partial rather than a full mismatch, thereby increasing the percentage sequence identity.

Conservative substitution tables providing functionally similar amino acids are well known in the art. Indeed, the following eight groups each contain amino acids that are conservative substitutions for one another: (1) Alanine (A), Glycine (G); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); (6) Phenylalanine (F), Tyrosine (Y), Tryptophan (W); (7) Serine (S), Threonine (T); and (8) Cysteine (C), Methionine (M).

When comparing (ribo)nucleic acids, similarity can also be determined. In this case, the similarity is appreciated at the codon level. Two codons are similar, if they are different codons specifying the same amino acid or if they are different codons specifying two similar amino acids.

In the present invention, a homolog of the ohrR gene is a gene or a nucleic acid presenting a similarity in the nucleotide sequence of at least 50%, at least 60%, at least 70%, at least 80%, at least 90% or at least 95% with the ohrR gene nucleotide sequence of *Bacillus cereus* ATCC14579.

In addition, a homolog of the ohrR gene product is a ribonucleic acid or a polypeptide presenting a similarity in the ribonucleotide or in the amino acid sequence of at least 50%, at least 60%, at least 70%, at least 80%, at least 90% or at least 95% with the ohrR gene product ribonucleotide or amino acid sequence of *Bacillus cereus* ATCC14579.

Advantageously, in the present invention, a homolog of the ohrR gene or of the ohrR gene product is a negative regulator belonging to the MarR family and is related to organic peroxide sensing, i.e. which is organic peroxide-inducible. This latter property can be checked by a disk diffusion assay well-known by the one skilled in the art and, particularly, by the disk diffusion assay using $H_2O_2$ as indicated chemical disclosed by Fuangthong et al., 2001 [10].

As for non exhaustive examples of OhrR homologs identified as previously explained i.e. by two iterations of PSI-BLAST (p value <1e-10), one can cite the protein of *Corynebacterium pseudogenitalium* ATCC 33035, the accession number of which is ZP_07715254.1; the protein of *Pseudomonas syringae* pv. *mori* str. 301020, the accession number of which is EGH21983.1; the protein of *Streptomyces sviceus* ATCC 29083, the accession number of which is ZP_06917482.1; the protein of *Arthrobacter aurescens* TC1, the accession number of which is YP 947034.1; the protein of *Myxococcus xanthus* DK1622, the accession number of which is YP_628922.1; and the protein of *Clostridium botulinium* B str. Eklund 17B, the accession number of which is YP_001887666.1.

The step (a) of the method according to the present invention consists in inactivating the ohrR gene or a homolog thereof or in inactivating the ohrR gene product or a homolog thereof.

Any process known by the one skilled in the art to inactivate a gene or a gene product can be utilized in the present invention. This latter employs routine techniques in the field of molecular biology. Basic texts disclosing the general methods useful for practicing the present invention include Sambrook and Russell, 2001 [11].

As used herein, the expression "inactivation of a gene" covers not only the inactivation stricto sensu but also refers to the alteration; partial, substantial, or complete deletion; silence or down-regulation of this gene. The terms and expressions "deletion", "partial deletion", "substantial deletion", "complete deletion", "eliminate", "elimination" and "knockout" can be utilized interchangeably.

In the context of the present invention, the inactivation of ohrR gene includes a structural alteration in the ohrR gene or locus that reduces or eliminates the production or activity of the ohrR gene product, i.e. the RNA or the polypeptide. In another embodiment, the genetically modified microorganism prepared at step (a) includes a structural alteration in a part of the microorganism genome different from the ohrR gene or locus that directly or indirectly reduces or eliminates the production or activity of the ohrR gene product, such as a structural alteration in a regulatory region that is not positioned within the ohrR gene or locus. By "ohrR locus", it must be understood a chromosomal locus comprising the ohrR gene.

The structural alteration can include, for example, a deletion, insertion or substitution in the ohrR gene, or other region that affects the production of the ohrR gene product. In a particularly preferred embodiment, the structural alteration includes a deletion, insertion or substitution in the coding region of the ohrR gene or locus. Deletion refers to the elimination of at least one nucleotide in a sequence. Insertion refers to the addition of at least one nucleotide in a sequence. Substitution refers to the change of at least one nucleotide in a sequence. A substitution can create a point mutation. In addition, a deletion, insertion or substitution can create a codon stop in the ohrR gene.

For example, the step (a) of the present invention method can provide a genetically modified microorganism that has an ohrR gene or locus which has been modified by deletion of a segment of the DNA of the ohrR gene or locus or insertion of a foreign DNA in the ohrR gene or locus or both.

Concerning the inactivation of the ohrR gene, a deletion of all or part of the ohrR gene or in the different part of the modified microorganism provides maximum stability because there is no opportunity for a reverse mutation to restore function.

In the present invention, the inactivation of the ohrR gene product can be obtained by introducing an exogenous agent into the microorganism to yield a modified microorganism, wherein the exogenous agent reduces or eliminates the production or activity of the ohrR gene product. The present invention is not limited by the nature of the exogenous agent supplied. This latter can be an interfering RNA (iRNA), an antisense DNA (asDNA), an antisense RNA (asRNA), double-stranded RNA (dsRNA), a ribozyme, a riboswitch, a DNA aptamer, a RNA aptamer, a peptide aptamer, a molecular inhibitor, a nucleic acid coding thereof or a vector or a plasmid comprising or operably encoding thereof.

A "molecular inhibitor" refers to a natural or synthetic molecule which inhibits the production or activity of the ohrR gene product. This molecular inhibitor can be a small organic molecule; a metabolite; a protein or peptide inhibitor such as a linear or cyclic peptide or a peptidomimetic; an antibody or a fragment thereof directed againt the polypeptide OhrR or against particular epitope present therein. A fragment of an antibody is advantageously chosen from Fab fragment, $F(ab')_2$ fragment, Fv fragment, scFv fragment and diabody.

Indeed, a way the activity of the OhrR polypeptide can be reduced is by interfering with the mRNA transcription product of the ohrR gene. For example, an exogenous agent such as a ribozyme or an expression vector operably encoding a ribozyme can be delivered to the microorganism to cleave the target mRNA, thereby reducing or eliminating production of the polypeptide. AsDNA, asRNA and dsRNA may also be used to interfere with translation.

In addition, one can inactivate the mRNA transcription product of the ohrR gene by adding a riboswitch before the translation start. Indeed, riboswitch RNA are able to sense specific metabolites and accordingly regulate production of proteins (see [12] and [13]).

Alternatively, the OhrR polypeptide or the OhrR protein can also be the target of the inactivation. Antibodies or antibody-like molecules such as peptide aptamers can be introduced into the microorganism to abolish the activity of the translated polypeptide, as can protein or peptide inhibitors such as linear or cyclic peptides, peptidomimetics, or small organic molecules.

The exogenous agent can be delivered or introduced into the microorganism by any routine methods known by the one skilled in the art such as an electroporation, a heat shock or/and a chemical process.

All the above explanations and details given for the inactivation of the ohrR gene or of the ohrR gene product apply to a gene homologous to the ohrR gene or to the gene product of a gene homologous to the ohrR gene mutatis mutandis. As a consequence, the expressions used hereinafter "ohrR gene (homolog)" means either "ohrR gene" or "ohrR gene homolog" and "ohrR gene (homolog) product" means either "ohrR gene product" or "ohrR gene homolog product".

The step (b) of the method according to the present invention consists in culturing the modified microorganism in particular culture conditions for the phenotype due to said modification (growth rate, biomass production and/or fermentative potential enhancement) to be expressed. These particular culture conditions are low-ORP anaerobic conditions.

The expression "growth conditions" and "culture conditions" are equivalent and can be used interchangeably. Similarly, the expression "growth medium" and "culture medium" are equivalent and can be used interchangeably.

The expression "anaerobic conditions" as used herein, means growth conditions in the absence of oxygen and notably refers to the absence of oxygen in the culture medium. In other words, the set-point dissolved oxygen tension value ($pO_2$) is below 0.2% in growth medium and, in particular, of 0% in growth medium. A $pO_2$ below 0.2% takes into account the traces of oxygen that can always be found in growth medium even under anaerobic conditions. Such $pO_2$ values can be achieved by continuously flushing the medium with either pure $N_2$ gas or with pure $H_2$ gas, optionally previously filtered.

The expressions "low-ORP", "low oxidation-reduction potential", "low oxidoreduction potential" and "low redox potential" are equivalent and can be used interchangeably. As used herein, the ORP and notably the low-ORP means the initial ORP and notably the initial low-ORP i.e. the ORP measured in the culture medium just before seeding or inoculating the modified microorganism in said medium. The ORP of a culture medium can be measured by any process known by the one skilled in the art. This measurement can utilize a sensor immersed in the culture medium or a redox-combined electrode such as the redox-combined electrode AgCl of Mettler Toledo and the measured values have to be corrected according to the reference electrode value, both electrodes being immersed in the culture medium.

In addition, as used herein, a low-ORP means a ORP inferior or equal to −100 mV, notably inferior or equal to −200 mV and, in particular, inferior or equal to −300 mV. A low-ORP can be obtain in the growth medium by introducing in said medium any known reducing agent in a appropriate quantity the one skilled in the art can calculate or determine by iteration. Various compounds may be used as a reducing agent. Among these, mention may be made of sulfites, sodium thioglycolate, dithiothreitol, ascorbic acid (vitamin C) and ammonia but also of reducing gases such as hydrogen or gaseous mixtures containing hydrogen.

In step (b) of the method according to the present invention, the modified microorganism can be cultured in a medium according to the usual method used for culturing microorganisms. This medium can be a commercial medium or an extemporaneously prepared medium.

As a medium used for culturing, the general nutritional medium containing a carbon source, a nitrogen source and inorganic salts can be used.

Any carbon source which can be assimilated by the modified microorganism is used. Examples include carbohydrates such as glucose, fructose, sucrose, molasses containing them; starch or starch hydrolysate; cellulose, lignocellulose or hemicellulose; one-carbon substrates; organic acids such as acetic acid or propionic acid; and alcohols such as ethanol and propanol.

Examples of suitable nitrogen source include ammonia; ammonium salts of inorganic acids or organic acids such as ammonium chloride, ammonium sulfate, ammonium acetate and ammonium phosphate; other nitrogen-containing compounds; peptone; meat extract; yeast extract; corn steep liquor; casein hydrolysate; soybean meal and soybean meal hydrolysate; and various cells obtained by fermentation and their digested products.

Examples of suitable inorganic salts include potassium dihydrogen phosphate, dipotassium hydrogen phosphate, magnesium phosphate, magnesium sulfate, sodium chloride, ferrous sulfate, manganese sulfate, copper sulfate and calcium carbonate.

The culturing temperature is typically from 15 to 40° C., and the pH during the culturing is typically maintained at 3.0 to 9.0. The pH can be adjusted using, for example, an inorganic or organic acid, an alkali solution, urea, calcium carbonate or ammonia. It must be pointed out that these general culture conditions can be slightly modified by the one skilled in the art relative to the microorganism cultured.

Advantageously, the cultured modified microorganisms are preferably in a suspension state. A "suspension" of cells is to be broadly understood as including all types of suspended or dispersed cell cultures; the term "suspension state" is thus used to distinguish cells that are not cultured in a liquid medium, such as cells cultured by way of adhering on a Petri dish. Thus, the term "suspension" includes both freely dispersed cells and agglomerated cells, regardless of whether agglomeration occurs spontaneously.

In addition, culture methods that can be utilized in the step (b) of the method according to the present invention include, but are not limited to, a batch culture, a continuous culture, or a "fed-batch" culture.

A "continuous (cell) culture" is a cell culture characterized by both a continuous inflow of a liquid nutrient feed and a continuous liquid outflow. Alternatively, a continuous culture may constitute a "perfusion culture" in which case the liquid outflow contains culture medium that is substantially free of cells, or substantially lower cell concentration than that in the bioreactor. In a perfusion culture, cells can be retained by, for example, filtration, centrifugation, or sedimentation.

A "fed-batch" culture is a batch cell culture to which substrate, in either solid or concentrated liquid form, is added either periodically or continuously during the run. Just as in a batch culture, a fed-batch culture is initiated by inoculating cells to the medium, but, in contrast to a batch culture, there is a subsequent inflow of nutrients, such as by way of a concentrated nutrient feed. In contrast to a continuous culture there is no systematic removal of culture fluid or cells from a fed-batch culture.

Thus, the present invention concerns a method for enhancing the growth rate, the biomass production and/or the fermentative potential of an anaerobic microorganism, comprising the steps consisting in:

a) modifying said anaerobic microorganism by inactivating the ohrR gene, the ohrR gene product or homolog thereof, a homolog to ohrR gene or to the ohrR gene product being a gene coding for an amino acid sequence, an amino acid sequence or a RNA coding for an amino acid sequence, wherein said amino acid sequence is detected using the OhrR amino acid sequence from *Bacillus cereus* by two iterations of Position Specific Iterated-BLAST (PSI-BLAST) (p value <1e-10);

b) culturing the modified anaerobic microorganism obtained in step (a) under low-ORP anaerobic conditions with a ORP inferior or equal to −100 mV;

thereby the growth rate, the biomass production and/or the fermentative potential of said modified microorganism is enhanced when compared with the growth rate, the biomass production and/or the fermentative potential of the corresponding non modified microorganism cultured under the same conditions.

The present invention provides a novel method for enhancing the anaerobic growth rate, the biomass production and/or the fermentative potential of microorganisms. These results with this increase can make it possible to obtain better yields for various and numerous industrial processes based on the use of a modified microorganism as previously defined in low-ORP anaerobic culture conditions.

Fields of application of the present invention are covering industrial processes related to human and animal health; agronomy and farming, agro-industries; marine and aquatic processes; chemical industry; energy industry and environmental processes.

As a consequence, the present invention concerns the use of a modified microorganism as previously defined, in low-ORP anaerobic culture conditions, in an industrial process related to human and animal health; agronomy and farming, agro-industries; marine and aquatic processes; chemical industry; energy industry and environmental processes.

More particularly, the present invention concerns the use of a modified microorganism as previously defined, in low-ORP anaerobic culture conditions, in the production of food products; in the production of biofuels; in the pharmaceutical field to produce active ingredients; in the production of valuable chemicals or in the destruction of hazardous and/or polluting chemicals.

Other characteristics and advantages of the present invention will additionally be apparent to the one skilled in the art on reading the examples below, which are given as an illustration and not a limitation, with reference to the attached figures.

SHORT DESCRIPTION OF THE DRAWINGS

FIG. 2 presents the specific uptake of glucose of the ΔohrR mutant and its parent strain *B. cereus* ATCC14579 (wt).

DETAILED DISCUSSION OF PARTICULAR EMBODIMENTS

I. Construction of ΔohrR Mutant.

*B. cereus* strains implemented in the experimental part are ATCC 14579 strains.

The ΔohrR cell mutant was constructed as disclosed hereinafter.

A BglII-SalI DNA fragment of 1,489 bp encompassing the ohrA and ohrR ORFs was amplified by PCR using chromosomal DNA as template and the primer pairs ohrmutF (5'-AGATCTTCTTATGAATCTGACAATCGGG-3', SEQ ID NO: 2 in the appended sequence listing) plus ohrmutR (5'-GTCGACCCGATAAAATTCCGAAAGGG-3', SEQ ID NO: 3 in the appended sequence listing).

The amplified DNA fragment was cloned into pCRXL-TOPO (Invitrogen). The resulting pCRXLohr plasmid was then digested with HpaI and BsgI. A 1.5 kb SmaI fragment containing the entire spectinomycin resistance gene spc was purified from the pDIA plasmid. This purified DNA fragment was ligated into BsgI-digested pCRXLohr. The resulting plasmid was digested with EcoRI and BglII. The resulting ohrR-spc fragment was subsequently inserted between the corresponding pMAD sites.

The resulting plasmid was introduced into *B. cereus* strain by electroporation. The ohrR gene was deleted by a double crossover event.

Chromosomal allele exchange was confirmed by PCR with oligonucleotide primers located upstream and downstream of the DNA regions used for allelic exchange. To confirm the nonpolar effect of the spectinomycin resistance cassette insertion in ohrR (which precedes ohrA in the ohrR-ohrA operon), fragments corresponding partially to ohrA and ohrA-ohrR intergenic region mRNA were amplified from total RNA isolated from ΔohrR cells as described above, thus confirming correct expression of the gene.

II. Analytical Procedures and Physiological Parameters.

*B. cereus* growth was monitored spectrophotometrically at 560 nm and calibrated against cell dry weight measurements, as previously described. Specific growth rate (μ) was determined using the modified Gompertz equation. Glucose, lactate, ethanol, formate, acetate and succinate concentrations were determined using commercial enzymatic kits (Diffchamb, Lyon, France; R-Biopharm, Saint-Didier au Mont-d'Or, France; Roche, Meylan, France).

Specific glucose consumption rate, defined as the differential change in glucose concentration with time, was calculated from the equation $q_{glucose}=\mu/Y_x$, where μ is the specific growth rate [$h^{-1}$] and $Y_x$, the biomass yield [g·mol carbon substrate$^{-1}$].

III. Growth Conditions.

Wild-type and ΔohrR *B. cereus* ATCC 14579 strains were grown at 37° C. in synthetic MOD medium supplemented with 30 mM glucose as carbon source as previously described [14].

The pH was maintained at 7.2 by automatic addition of 2N KOH. The temperature and pH regulated batch was equipped with a Mettler Toledo polarographic oxygen electrode coupled with feedback regulation to maintain the set-point dissolved oxygen tension value ($p0_2$) via air sparging and agitation speed. The bioreactor was spurge with air alone to set a $PO_2$ value of 100%. A $pO_2$ of 0% was obtained by continuously flushing the medium at 20 ml/h with either pure $N_2$ gas or with pure $H_2$ gas previously filtered through a Hungate column.

Oxidoreduction potential (ORP) was measured using a redox-combined electrode (AgCl, Mettler Toledo) and the values were corrected according to the reference electrode value ($E_{ref}$=+200 mV at 37° C.).

Each bioreactor was inoculated with a subculture grown overnight under aerobiosis or anaerobiosis in MOD medium supplemented with carbon source and the required electron acceptors. A sample of the overnight culture was diluted in fresh medium to achieve an initial optical density of the culture at 560 nm of 0.02. Cells were harvested by centrifugation at the early-exponential growth phase, i.e. 1.5 h after reaching the maximal growth rate (when μ=80 (±10) % of $\mu_{max}$,) and immediately frozen at −80° C. until analysis. Supernatants were kept to perform metabolite and glucose assays.

IV. Results.

Figure 1:
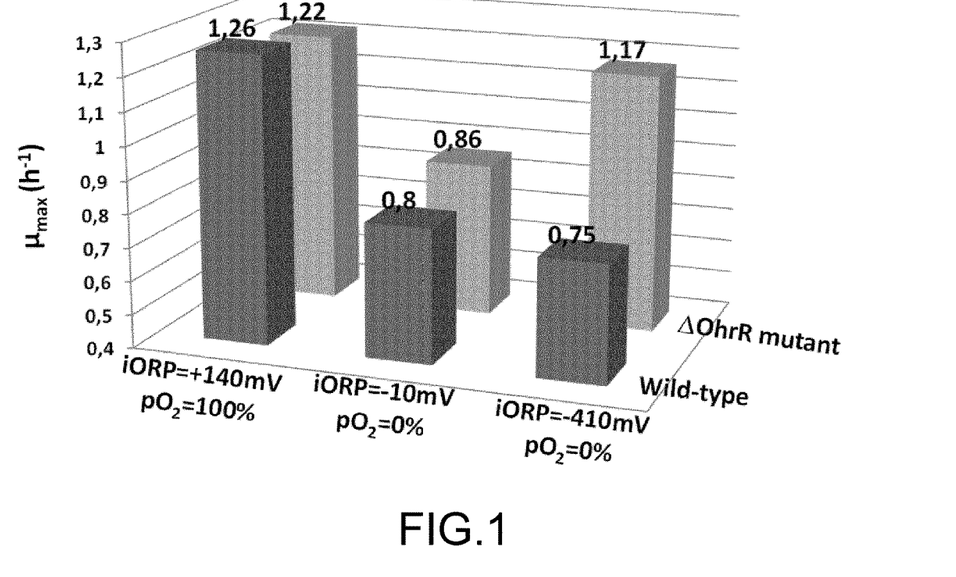
FIG. 1 presents the physiological parameters for controlled batch cultures of the ΔohrR mutant and its parent strain *B. cereus* ATCC14579 (wt).

The disruption of ohrR led to a significant increase (~1.6-fold) of the growth rate of fermentative cells under low-ORP conditions compared with wild-type cells (Table 1 hereinafter; FIG. 1).

Figure 2:
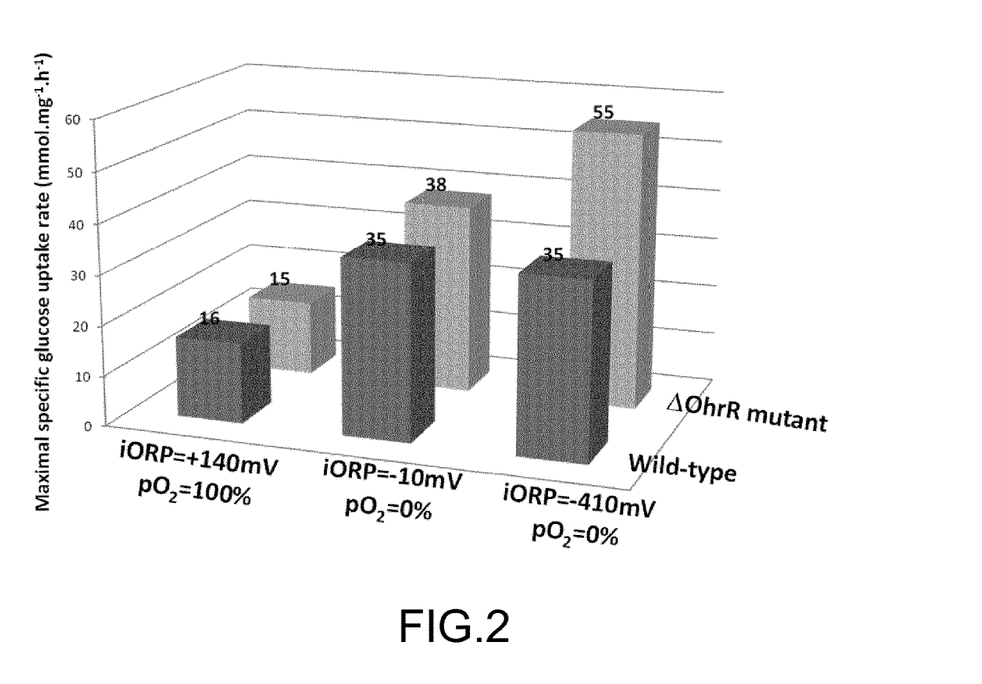

No significant differences between the two strains could be observed under high-ORP anaerobiosis and aerobiosis. The higher growth rate under low-ORP conditions results from a higher carbon flow through glycolysis, as reflected by the higher glucose uptake rate (FIG. 2) and subsequently from a higher ATP production (Table 1).

TABLE 1

Physiological parameters for controlled batch cultures of the ΔohrR mutant and its parent strain *B. cereus* ATCC14579 (wt).

| | Growth | | | | | |
|---|---|---|---|---|---|---|
| | Anaerobic fermentative | | | | Aerobic | |
| | iORP | | | | | |
| | −410 mV | | −10 mV | | +140 mV | |
| Strain | WT | ΔohrR | WT | ΔohrR | WT | ΔohrR |
| $\mu_{max}$ (h$^{-1}$) | 0.75 ± 0.05 | 1.17 ± 0.01 | 0.80 ± 0.07 | 0.86 ± 0.02 | 1.26 ± 0.12 | 1.22 ± 0.18 |
| $Y_x$ | 21 ± 1 | 21 ± 1 | 23 ± 1 | 23 ± 1 | 8 ± 1 | 8 ± 1 |
| $q_{glucose}$ | 35 ± 2 | 55 ± 5 | 35 ± 2 | 38 ± 2 | 16 ± 2 | 15 ± 2 |
| $Y_{Lactate}$ | 0.68 ± 0.05 | 0.66 ± 0.15 | 0.48 ± 0.12 | 0.63 ± 0.15 | nz | nz |
| $Y_{Acetate}$ | 0.12 ± 0.02 | 0.20 ± 0.04 | 0.14 ± 0.04 | 0.15 ± 0.04 | 0.14 ± 0.01 | 0.20 ± 0.04 |
| $Y_{Formate}$ | 0.05 ± 0.01 | 0.13 ± 0.07 | 0.04 ± 0.02 | 0.05 ± 0.03 | nz | nz |
| $Y_{Ethanol}$ | 0.070 ± 0.005 | 0.10 ± 0.02 | 0.054 ± 0.006 | 0.07 ± 0.01 | nz | nz |
| $Y_{ATP}$ | 1.98 | 1.62 | 2.00 | nd | nd | nd |
| NADH recovery | 1.2 | 1.2 | 1.5 | 1.5 | nd | nd |

Cells were grown under H$_2$ and N$_2$-generated anaerobiosis (iORP = −410 mV and −10 mV, respectively; pO$_2$ = 0%) and full aerobiosis (iORP = +140 mV; pO$_2$ = 100%;). Data are the means of triplicate measures obtained from three independent cultures.

Abbreviations:

$\mu_{max}$, specific growth rate determined by measurement of the dry weight;

$Y_x$, biomass yield on glucose (gram of biomass per gram of glucose consumed);

$q_{glucose}$, millimoles of glucose consumed per milligram of biomass per hour;

$Y_{lactate}$, $Y_{acetate}$, $Y_{ethanol}$ and $Y_{formate}$, moles of metabolite produced per moles of glucose consumed measured at $\mu_{max}$;

nz, near zero;

nd, not determined.

NADH recovery was calculated at the ratio of pathways producing NADH versus those consuming NADH (producing NAD$^+$).

The data obtained by the inventors also indicate that disruption of ohrR allows i) lactate production to reach its apogee in terms of quantity under high-ORP fermentative conditions and ii) formate, ethanol and acetate to reach their apogee in terms of quantity under low-ORP conditions.

The high-throughput proteomic data obtained by the inventors (not described here) point at i) the role of OhrR in proteome remodeling when oxygen is lacking, and more specifically when anoxic-ORP is decreasing and, ii) its regulatory impact on activity of main central metabolism pathways. Through the control of proteome change, OhrR strangles the fermentative potential of *B. cereus* and restricts cell growth under low-ORP anaerobiosis while ensuring a high synthesis of chemotaxis and motility proteins. Inactivation of the ohrR gene or its product results in higher fermentative potential under these conditions.

REFERENCES

1. International application WO 2009/101328 in the name of L'AIR LIQUIDE SOCIETE ANONYME POUR L'ETUDE ET L'EXPLOITATION DES PROCEDES GEORGES CLAUDE and published on Aug. 20, 2009.
2. Patent application FR 2 635 788 in the names of Institut Pasteur and Centre National de la Recherche Scientifique and published on Mar. 2, 1990.
3. Patent application FR 2 778 922 in the name of Institut Pasteur and published on Nov. 26, 1999.
4. International application WO 2011/018116 in the name of ALGENOL BIOFUELS Inc. and published on Feb. 17, 2011.
5. International application WO 2011/006136 in the name of VERDEZYNE Inc. and published on Jan. 13, 2011.
6. Article by Duport et al., 2006, J. Bacteriol., vol. 188, pages 6640-6651.
7. Article by Gao et al., 2010, Protein Cell, vol. 1, pages 621-626.
8. Article by Gibson et al., 2010, Science, vol. 329, pages 52-56.
9. Article by Duarte and Latour, 2010, Molecular BioSystems, vol. 6, pages 316-323.
10. Article by Fuangthong et al., 2001, J. Bacterial., vol. 183, pages 4134-4141.
11. Sambrook and Russell, 2001, Molecular Cloning, A Laboratory Manual ($3^{rd}$ edition).
12. Article by Dambach and Winkler, 2009, Curr. Opin. Microbial., vol. 12, pages 161-169.
13. Article by Henkin, 2008, Genes Dev., vol. 22, pages 3383-3390.
14. Article by Clair et al., 2010, Mol. Cell. Proteomics, vol. 9, pages 1486-1498.

The invention claimed is:

1. A method for enhancing growth rate, biomass production, fermentative potential, or any combination thereof, of an anaerobic microorganism, the method comprising:

modifying the anaerobic microorganism by inactivating an organic hydroperoxide resistance Regulator (ohrR) gene, an ohrR gene product or a homolog thereof, to obtain a modified anaerobic microorganism, wherein the homolog of the ohrR gene is a gene or a nucleic acid presenting an identity in the nucleotide sequence of at least 20% with the ohrR gene nucleotide sequence encoding the ohrR gene product of *Bacillus cereus* ATCC14579 of SEQ ID NO: 1, wherein the homolog of the ohrR gene product is a ribonucleic acid encoding an OhrR polypeptide or is an OhrR polypeptide presenting an identity in the amino acid sequence of at least 20% with the amino acid sequence of *Bacillus cereus* ATCC 14579 of SEQ ID NO: 1, and wherein the homolog of the ohrR gene encodes or of the ohrR gene product is an organic peroxide-inducible negative regulator belonging to the MarR family repressor proteins; and culturing the modified anaerobic microorganism under low Oxido-Reduction Potential (ORP) anaerobic conditions with the ORP less than or equal to −100 mV;

thereby which the growth rate, the biomass production, the fermentative potential, or any combination thereof, of the modified anaerobic microorganism is enhanced when compared with the growth rate, the biomass production, the fermentative potential, or any combination thereof, of a corresponding non modified microorganism cultured under the same conditions.

2. The method according to claim 1, wherein the anaerobic microorganism is a facultative anaerobic microorganism or an obligate anaerobic microorganism.

3. The method according to claim 1, wherein the anaerobic microorganism is a natural, genetically-modified or synthetic, eukaryotic or prokaryotic, anaerobic microorganism.

4. The method according to claim 1, wherein the homolog of the ohrR gene is a gene or a nucleic acid presenting an identity in the nucleotide sequence of at least 20% with the ohrR gene nucleotide sequence encoding the ohrR gene product of *Bacillus cereus* ATCC14579 of SEQ ID NO: 1.

5. The method according to claim 1, wherein the homolog of the ohrR gene product is a ribonucleic acid encoding an OhrR polypeptide or is an OhrR polypeptide presenting an identity in the amino acid sequence of at least 30% with the amino acid sequence of *Bacillus cereus* ATCC14579 of SEQ ID NO: 1.

6. The method according to claim 1, wherein the inactivation of the ohrR gene comprises a structural alteration in the ohrR gene or locus that reduces or eliminates the production or activity of the ohrR gene product.

7. The method according to claim 1, wherein the inactivation of the ohrR gene comprises a structural alteration in a part of the anaerobic microorganism genome different from the ohrR gene or locus that directly or indirectly reduces or eliminates the production or activity of the ohrR gene product.

8. The method according to claim 1, wherein the inactivation of the ohrR gene product is obtained by introducing an exogenous agent into the anaerobic microorganism to yield the modified anaerobic microorganism, wherein the exogenous agent reduces or eliminates the production or activity of the ohrR gene product.

9. The method according to claim 8, wherein the exogenous agent is selected from the group consisting of an interfering RNA (iRNA), an antisense DNA (asDNA), an antisense RNA (asRNA), double-stranded RNA (dsRNA), a ribozyme, a riboswitch, a DNA aptamer, a RNA aptamer, a peptide aptamer, a molecular inhibitor, a nucleic acid coding thereof or a vector, and a plasmid comprising or operably encoding thereof.

10. The method according to claim 1, wherein the ORP is less than or equal to −200 mV.

11. The method according to claim 1, wherein the modified anaerobic microorganism is suitable in low-ORP anaerobic culture conditions with the ORP less than or equal to −100 mV, in an industrial process related to human and animal health, agronomy, farming, agro-industries, marine and aquatic processes, chemical industry, energy industry and environmental processes.

12. The method according to claim 1, wherein the modified anaerobic microorganism is suitable in low-ORP anaerobic culture conditions with the ORP less than or equal to −100 mV, in the production of food products, in the production of biofuels, in the pharmaceutical field to produce active ingredients, in the production of valuable chemicals or in the destruction of hazardous chemicals, polluting chemicals, or any combination thereof.

13. The method according to claim 1, wherein the inactivation of the ohrR gene homolog comprises a structural alteration in the ohrR gene homolog or locus that reduces or eliminates the production or activity of the ohrR gene homolog product.

14. The method according to claim 1, wherein the inactivation of the ohrR gene homolog comprises a structural alteration in a part of the anaerobic microorganism genome different from the ohrR gene homolog or locus that directly or indirectly reduces or eliminates the production or activity of the ohrR gene homolog product.

15. The method according to claim 1, wherein the inactivation of the ohrR gene homolog product is obtained by introducing an exogenous agent into the anaerobic microorganism to yield the modified anaerobic microorganism, wherein the exogenous agent reduces or eliminates the production or activity of the ohrR gene homolog product.

16. The method according to claim 1, wherein the ORP is less than or equal to −300 mV.

* * * * *

SEQUENCE LISTING

<160> NUMBER OF SEQ ID NOS: 3

<210> SEQ ID NO 1
<211> LENGTH: 150
<212> TYPE: PRT
<213> ORGANISM: Bacillus cereus ATCC14579
<220> FEATURE:
<221> NAME/KEY: PEPTIDE
<222> LOCATION: (1)..(150)
<223> OTHER INFORMATION: Protein OhrR

<400> SEQUENCE: 1

Met Thr Glu Asp Ser Leu His Leu Asp Asn Gln Leu Cys Phe Ser Ile
1               5                   10                  15

Tyr Ala Cys Ser Arg Glu Val Thr Arg Phe Tyr Arg Pro Tyr Leu Glu
            20                  25                  30

Glu Met Gly Ile Thr Tyr Pro Gln Tyr Ile Thr Leu Leu Val Leu Trp
        35                  40                  45

Glu Gln Asp Gly Leu Thr Val Lys Glu Ile Gly Glu Arg Leu Phe Leu
    50                  55                  60

Asp Ser Gly Thr Leu Thr Pro Met Leu Lys Arg Met Glu Ser Leu Asn
65                  70                  75                  80

Leu Val Lys Arg Val Arg Ser Lys Glu Asp Glu Arg Lys Val Cys Ile
                85                  90                  95

Glu Leu Thr Glu Gln Gly Lys Asp Leu Gln Asp Lys Ala Cys Ser Leu
            100                 105                 110

Pro Thr Thr Met Ala Thr Asn Leu Gly Ile Thr Glu Gln Glu Tyr Arg
        115                 120                 125

Ser Leu Leu Ile Gln Leu Asn Lys Leu Ile Glu Thr Met Lys Thr Ile
    130                 135                 140

Asn Asp Arg Lys Gly Glu
145                 150

<210> SEQ ID NO 2
<211> LENGTH: 28
<212> TYPE: DNA
<213> ORGANISM: Unknown
<220> FEATURE:
<223> OTHER INFORMATION: Artificial sequence
<220> FEATURE:
<221> NAME/KEY: misc_feature
<222> LOCATION: (1)..(28)
<223> OTHER INFORMATION: Primer ohrmutF

<400> SEQUENCE: 2
agatcttctt atgaatctga caatcggg                                    28

<210> SEQ ID NO 3
<211> LENGTH: 26
<212> TYPE: DNA
<213> ORGANISM: Unknown
<220> FEATURE:
<223> OTHER INFORMATION: Artificial sequence
<220> FEATURE:
<221> NAME/KEY: misc_feature
<222> LOCATION: (1)..(26)
<223> OTHER INFORMATION: Primer ohrmutR

<400> SEQUENCE: 3
gtcgacccga taaaattccg aaaggg                                      26